(12) United States Patent
Moyer

(10) Patent No.: US 7,887,733 B2
(45) Date of Patent: Feb. 15, 2011

(54) METHOD OF MAKING A PEEL-AWAY INTRODUCER

(75) Inventor: Robert Moyer, Walnutport, PA (US)

(73) Assignee: B. Braun Medical, Inc., Allentown, PA (US)

( * ) Notice: Subject to any disclaimer, the term of this patent is extended or adjusted under 35 U.S.C. 154(b) by 156 days.

(21) Appl. No.: 12/362,116

(22) Filed: Jan. 29, 2009

(65) Prior Publication Data

US 2009/0218728 A1  Sep. 3, 2009

Related U.S. Application Data

(62) Division of application No. 10/935,207, filed on Sep. 7, 2004, now Pat. No. 7,524,305.

(51) Int. Cl.
*B29C 45/14* (2006.01)

(52) U.S. Cl. .................. 264/273; 264/275; 425/127; 425/129.1

(58) Field of Classification Search .................. None
See application file for complete search history.

(56) References Cited

U.S. PATENT DOCUMENTS

| 4,218,930 | A | * | 8/1980 | Naito et al. | 476/73 |
|---|---|---|---|---|---|
| 4,338,278 | A | * | 7/1982 | Schultz | 264/261 |
| 4,581,025 | A | | 4/1986 | Timmermans | |
| 4,596,559 | A | | 6/1986 | Fleischhacker | |
| 5,125,904 | A | | 6/1992 | Lee | |
| 5,167,634 | A | | 12/1992 | Corrigan, Jr. et al. | |
| 5,312,355 | A | | 5/1994 | Lee | |
| 5,672,405 | A | * | 9/1997 | Plank et al. | 428/133 |
| 5,683,641 | A | * | 11/1997 | Jaskowiak | 264/267 |
| 5,762,637 | A | * | 6/1998 | Berg et al. | 604/264 |
| 6,083,207 | A | | 7/2000 | Heck | |
| 6,358,460 | B1 | * | 3/2002 | Hunt et al. | 264/491 |
| 6,511,232 | B1 | * | 1/2003 | Ishii et al. | 385/78 |
| 6,692,464 | B2 | * | 2/2004 | Graf | 604/160 |
| 2003/0163139 | A1 | | 8/2003 | Graf | |
| 2004/0254534 | A1 | | 12/2004 | Bjorkman et al. | |
| 2006/0041230 | A1 | * | 2/2006 | Davis | 604/160 |

OTHER PUBLICATIONS

Int'l Search Report for Int'l Application No. PCT/US05/13678, dated Jun. 25, 2006.

* cited by examiner

*Primary Examiner*—Edmund H. Lee
(74) *Attorney, Agent, or Firm*—RatnerPrestia

(57) ABSTRACT

A device and method of making a peel-away introducer sheath adapted for use in transcutaneous insertions of medical instrumentation according to an embodiment of the present invention includes, forming at least two anchor apertures in an end portion of a peel-away sheath tube, molding a fitting around the end portion by passing molten resin into a fitting mold and through the at least two anchor apertures, and cooling the resin within the mold and the at least two anchor apertures to thereby fasten the fitting to the sheath tube.

16 Claims, 7 Drawing Sheets

METHOD OF MAKING A PEEL-AWAY INTRODUCER

RELATED APPLICATIONS

This is a divisional application of U.S. application Ser. No. 10/935,207 filed Sep. 7, 2004, the contents of which are incorporated by reference herein for all purposes.

FIELD OF THE INVENTION

The present invention relates generally to medical devices and more particularly to an introducer sheath for assisting transcutaneous insertion of catheters or medical probes.

BACKGROUND OF THE INVENTION

Introducer sheaths are commonly used in various medical procedures where a catheter is transcutaneously introduced into an interior body lumen or cavity, such as a blood vessel or a hollow body organ. Typically, the introducer sheath comprises a thin-walled sheath tube that is introduced through a previously formed needle penetration. The introducer sheath can be introduced together with an internal stylet or obturator, where the stylet or obturator has a tapered distal end that extends from the sheath and dilates the previously formed hole as the sheath is advanced. After the combination of the sheath and stylet/obturator has been introduced, the stylet/obturator is removed, leaving a working access lumen defined by the sheath. Catheters and other working devices can then be introduced through the access lumen to perform various medical procedures.

It may be desirable to remove the sheath and leave the catheter resident in the artery or vein. Unfortunately, conventional sheaths have a drawback in that typically they cannot be withdrawn after insertion of a catheter or other device. Most catheters terminate at enlarged hubs which prevent conventional sheaths from sliding off over the end. The sheath, therefore, must remain resident in the vein or artery throughout the procedure.

A known solution is a peel-away or splittable sheath. Generally, peelable sheaths permit removal of the sheath after insertion because it is not necessary for them to pass over the hub of the catheter. Peelable sheaths provide advantages over prior sheaths. The sheath must be constructed of a smooth biocompatible material with a low coefficient of friction. These materials are typically chemical resistant. However, known peelable sheaths also have drawbacks. Peelable sheaths are more flexible than their predecessors and, thus, are not as responsive to manipulation, e.g., during insertion. This is particularly true for peelable sheaths having tabs preformed by open ended slits, because once the tabs are formed, the sheath loses much of its structural integrity.

The material of the sheath also presents a challenge to its manufacturers. The sheath must be constructed of a smooth biocompatible material with a low coefficient of friction. These materials are typically chemical resistant. More importantly, when the sheath is a peelable sheath, the material must be easily splittable but still retain some structural rigidity. Additionally, because the sheath material must have the above qualities, adhering a fitting to the sheath can be difficult.

SUMMARY OF THE INVENTION

The present invention is directed to a peel-away introducer sheath with a fitting and its method for making. The method of making the peel-away introducer sheath adapted for use in the transcutaneous insertions of medical instrumentation according to an embodiment of the present invention includes forming at least two anchor apertures in an end portion of a peel-away sheath tube, molding a fitting around the end portion by passing molten resin into a fitting mold and through the at least two anchor apertures, and cooling the resin within the mold and the at least two anchor apertures to thereby fasten the fitting to the sheath tube.

Another embodiment of the method for making a tear-away introducer of the present invention having a sheath tube splitable along at least one longitudinal axis of the tube and a fitting in a contiguous mechanical connection with the sheath includes forming at least two anchor apertures in an end portion of the peel-away sheath tube, inserting an inner mold portion having at least two channels defining respective flow paths into the end portion of the sheath, aligning channels of the inner mold portion with the anchor apertures of the sheath so that defined flow paths are in fluid communication with the apertures of the inner mold, forming an outer mold portion around the inner mold portion inserted into the end portion of the sheath tube, passing molten resin into the outer mold portion so that molten resin flows through the flow paths and the respective anchor aperture, and cooling the resin within the outer mold portion and the at least two anchor apertures to fasten the fitting to the sheath tube in a contiguous mechanical connection.

A peel-away introducer sheath of the present invention has a splitable sheath adapted for use in the transcutaneous insertion of medical instrumentation. The sheath has a longitudinal axis and at least two anchor apertures disposed on an end portion of the sheath. The at least two anchor apertures have a central axis, which is substantially perpendicular to the longitudinal axis of the sheath. Disposed on the end portion of the sheath is a fitting. The fitting has at least two wing portions attached to a central body. The central body of the fitting also has at least one line of weakness. The central body is adapted to engage the sheath through the at least two anchor apertures.

A peel-away introducer sheath according to another embodiment of the present invention includes a splitable sheath, adapted for use in the transcutaneous insertion of medical instrumentation. The sheath has a longitudinal axis and at least two anchor apertures disposed on the end portion of the sheath. The at least two anchor apertures have a central axis which is substantially perpendicular to the longitudinal axis of the sheath. The introducer also has a fitting disposed on the end portion of the sheath. The fitting has at least two wing portions attached to its central body. The central body of the fitting has at least one line of weakness and, disposed therein, a resealable membrane. The fitting is connected to the sheath through the at least two anchor apertures in a contiguous mechanical connection.

DETAILED DESCRIPTION OF EXEMPLARY EMBODIMENTS OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
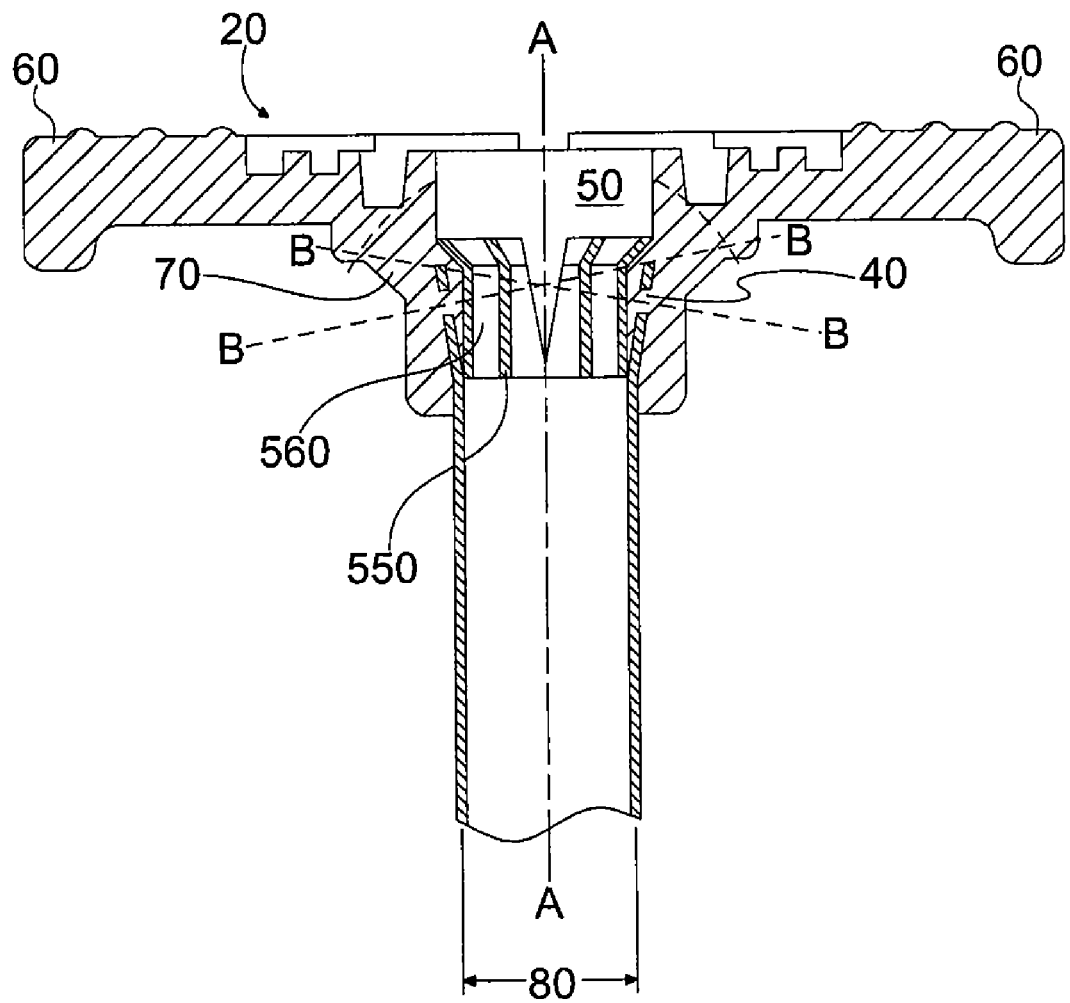
FIG. 1 is a cut-away side view of the sheath introducer of FIG. 1 with an inner mold portion.
Figure 4:
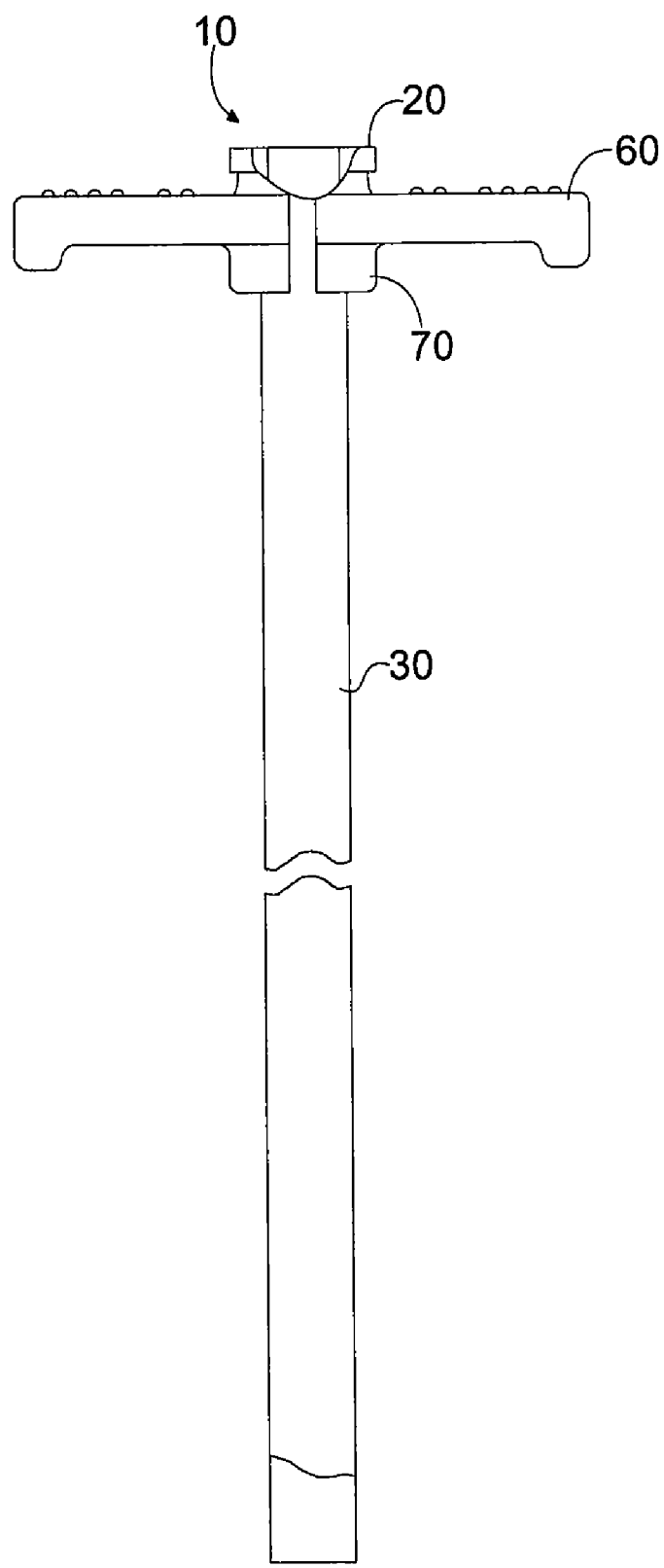
FIG. 4 illustrates a peel away sheath introducer in accordance with the present invention.

Referring now to the figures where like numerals represent like features, FIG. 4 illustrates peel-away introducer sheath 10 adapted for use in the transcutaneous insertion of medical instrumentation. FIG. 1 illustrates in more detail peel-away introducer sheath 10 having fitting 20 coupled with sheath tube 30. Sheath tube 30 and fitting 20 define a continuous lumen access having a longitudinal axis line A-A. Sheath tube 30 defines at least two anchor apertures 40 disposed at an end portion of sheath tube 30. At least two anchor apertures 40 have a central axis line B-B that is substantially perpendicular to longitudinal axis line A-A of sheath tube 30 and fitting 20. Fitting 20 is disposed on the end portion of sheath tube 30 and has at least two wing portions 60 attached to central body 70 having at least one line of weakness (not shown in FIG. 1). Central body 30 is adapted to engage, and connect to, sheath tube 30 through at least two anchor apertures 40. FIG. 1 also shows inner mold portion 50 inserted within fitting 20 and sheath tube 30.

Sheath tube 30, according to the embodiment of the peel-away introducer sheath shown in FIG. 1, has a diameter 80 and at least two anchor apertures 40 to form a mechanical connection with fitting 20. Although any number of anchor apertures may be used to impart the desired connective strength between sheath tube 30 and fitting 20, sheath tube 30 preferably has six anchor apertures. Anchor apertures 40 connect sheath tube 30 to fitting 20 at central body 70. The mechanical connection formed is impervious to air and other fluids, not by fusion of fitting 20 with sheath tube 30, but through a contiguous mechanical connection of central body 70 to sheath tube 30 through apertures 40. According to an embodiment of the present invention, anchor apertures 40 are substantially circular. The shape of anchor apertures 40, may, however, have a shape other than substantially circular. For example, anchor apertures 40 may be square, diamond, oval, or even random. Sheath tube 30 may also have a score line or a pre-formed tear line along at least one longitudinal line along the circumference of sheath tube 30. If the sheath tube has a pre-formed tear line, the pre-formed tear runs substantially parallel with longitudinal axis line A-A and is disposed at the aperture end. If sheath tube 30 is scored, for example in a perforated line, the score line runs substantially parallel to longitudinal axis line A-A and along substantially the entire length of sheath tube 30. The score line or pre-formed tear line allows sheath tube 30 to be peeled away more easily depending on the material of sheath tube 30.

Figure 2:
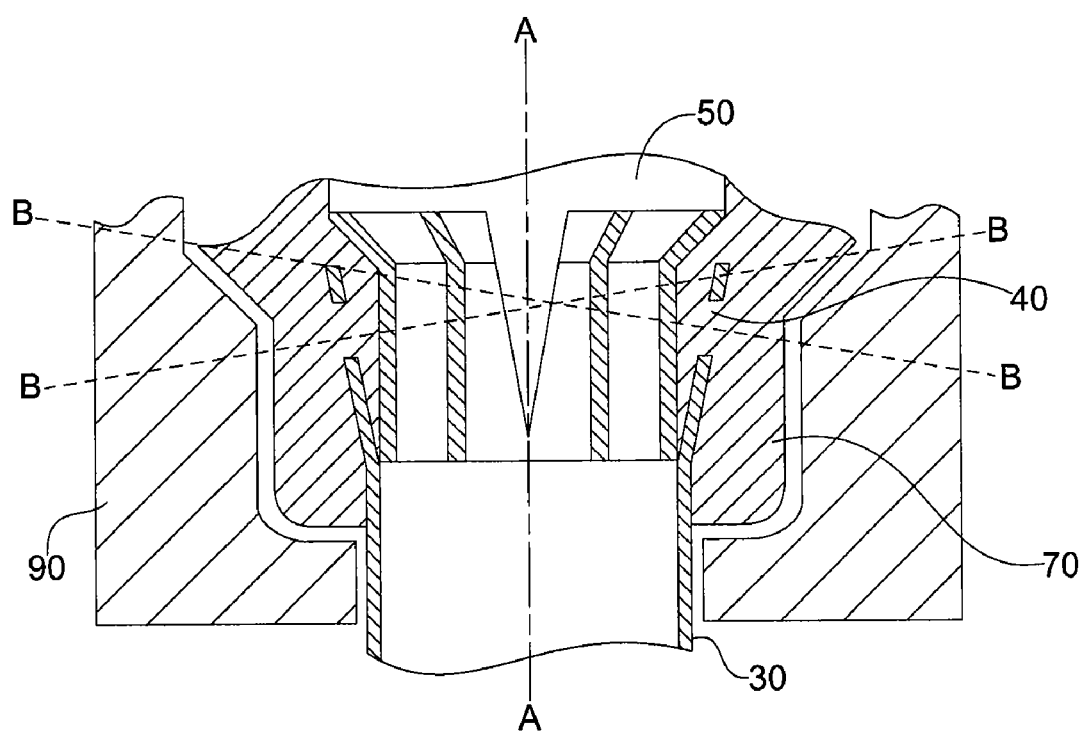
FIG. 2 is an enlarged view of a portion of that which is shown in FIG. 1.

FIG. 2 is an enlarged cut-away side view of the connection between central body 70 of fitting 20 and sheath tube 30. Also shown in FIG. 2 is inner mold portion 50 inserted into sheath tube 30 and surrounded in part by outer mold 90, discussed below in more detail. Peel-away introducer sheath 10, formed by fitting 20 and sheath tube 30, define a continuous lumen having longitudinal access A-A. Anchor apertures 40 of sheath tube 30 also have an axis B-B that is substantially perpendicular to longitudinal axis A-A. Preferably, the central axis of the apertures with respect to the longitudinal axis of the sheath tube intersects the longitudinal axis line A-A of the sheath tube at an angle of about 90° +/−20°. As shown in FIG. 2, central body 70 forms the exterior of fitting 20 and is in fluid communication with inside wall of access lumen through anchor apertures 40.

Sheath tube 30 may be constructed of any biocompatible material suitable for use in medical procedures. Sheath tube 30 may be a thermoset or thermoplastic resin. Exemplary thermosetting resins include unsaturated polyester, vinyl ester, epoxy, urethane, and phenolic. Preferably, sheath tube 30 is polytetrafluoroethylene.

Polytetrafluoroethylene or PTFE is formed by the addition polymerization of tetrafluoroethylene, $CF_2=CF_2$ (tetrafluoroethene). PTFE has a lineal molecular structure particularly suited for the present invention. Because its molecular structure is linear, PTFE can be torn or split along is molecular axis in a substantially straight line without any scoring or pre-forming of a tear line. PTFE also maintains its physical properties over a large temperature range, −270° to 385° C. These properties make it especially useful as a sheath tube because the sheath tube will contact human skin and tissue and the slippery surface aides in the initial insertion of the introducer sheath into the human body.

Exemplary thermoplastic resins are polypropylene, polyethylene, polystyrene, acrylonitrile-butadiene-styrene (ABS), nylon, polycarbonate, thermoplastic polyester, polyphenylene oxide, polysulfone and poly-ether-ether-ketone (PEEK).

Figure 3:
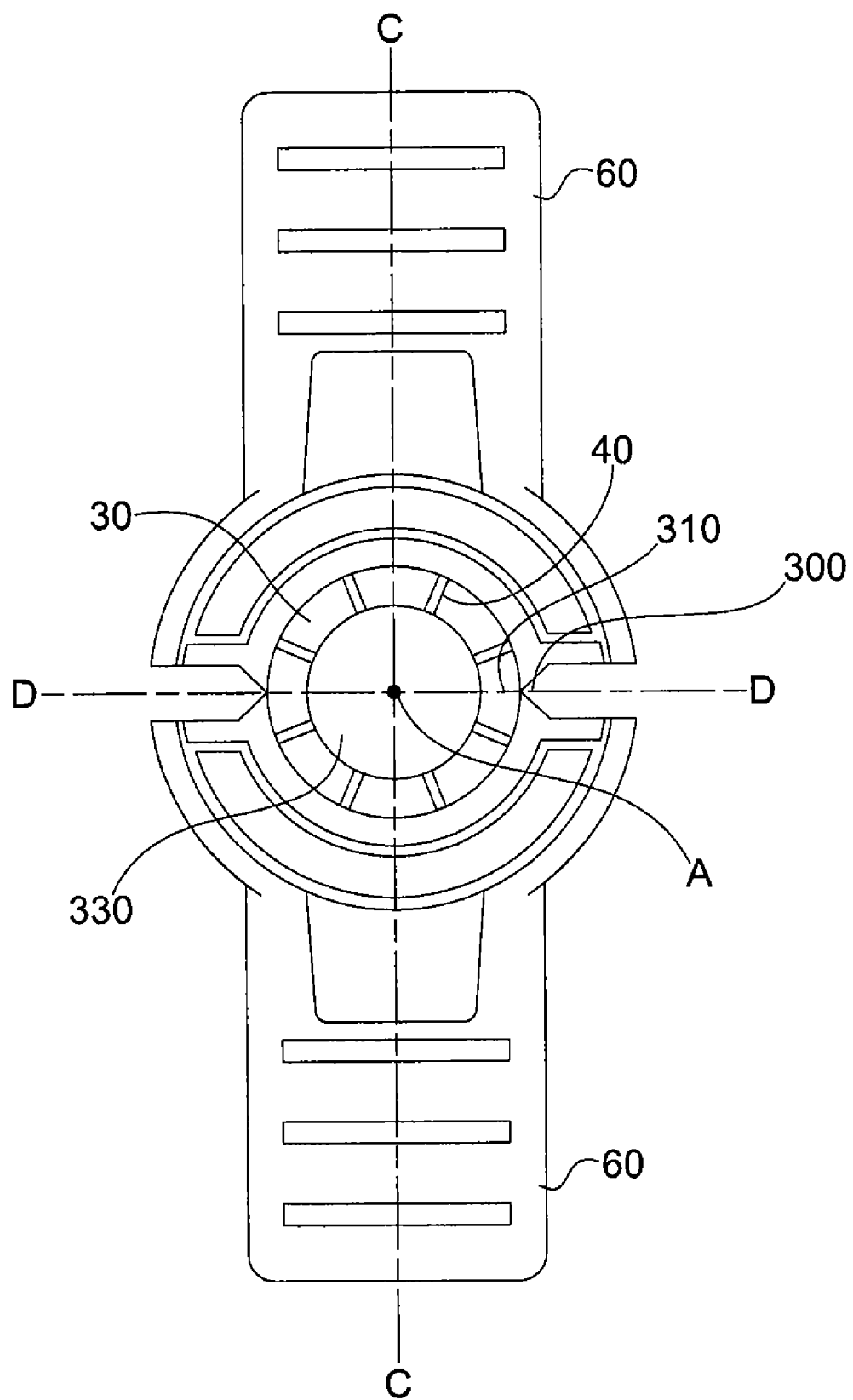
FIG. 3 is a top view of the sheath introducer of FIG. 1.

FIG. 3 is a top view along longitudinal axis A-A (shown by point A) of a peel-away introducer sheath 10. Shown in the embodiment of FIG. 3, peel-away introducer sheath has two apposing wing portions 60 defining axis C-C coupled to central body 70. Although two wing portions 60 are desirable, any number of wing portions may be used. Substantially perpendicular to axis C-C is axis D-D. Axis D-D defines at least one line of weakness 300 of fitting 20. According to an embodiment of the present invention and depending on the material of the sheath tube, sheath tube 30 may have a score line 310 that runs parallel along sheath tube 30. When peel-away introducer sheath 10 is formed, score line 320 runs substantially co-linearly with at least one line of weakness 300 of fitting 20. As discussed above, however, when sheath tube 30 is the preferred material, polytetrafluoroethylene, no score line is needed.

Fitting 20 may be formed from an injectable thermoplastic resin. Such a resin should be composed of a biocompatible material suitable for use in medical procedures. The resin chosen also should facilitate manufacture using, e.g., extrusion or injection molding techniques. However, it will be appreciated that the materials and manufacturing methods may vary depending on the application.

Referring again to FIG. 3, fitting 20 also has resealable membrane 330 disposed over the longitudinal access lumen of peel-away introducer sheath 10. Resealable membrane 330 may be punctured repeatedly by the secondary medical devices inserted into lumen access. When the secondary medical devices are removed, resealable membrane self-seals to prevent fluids from escaping.

According to another embodiment of the present invention, a peel-away introducer sheath has a splitable sheath adapted for use in the transcutaneous insertion of medical instrumentation. Sheath 30 has longitudinal axis line A-A and at least two anchor apertures 40 disposed on an end portion of sheath 30. At least two anchor apertures 40 have central axis line B-B substantially perpendicular to longitudinal axis line A-A of sheath 30. Fitting 20 is disposed on the end portion of sheath 30 and includes at least two wing portions 60 attached to central body 70 having at least one line of weakness 300, resealable membrane 330, and is adapted to engage sheath 30 through at least two anchor apertures 40 in a contiguous mechanical connection.

Figure 7:
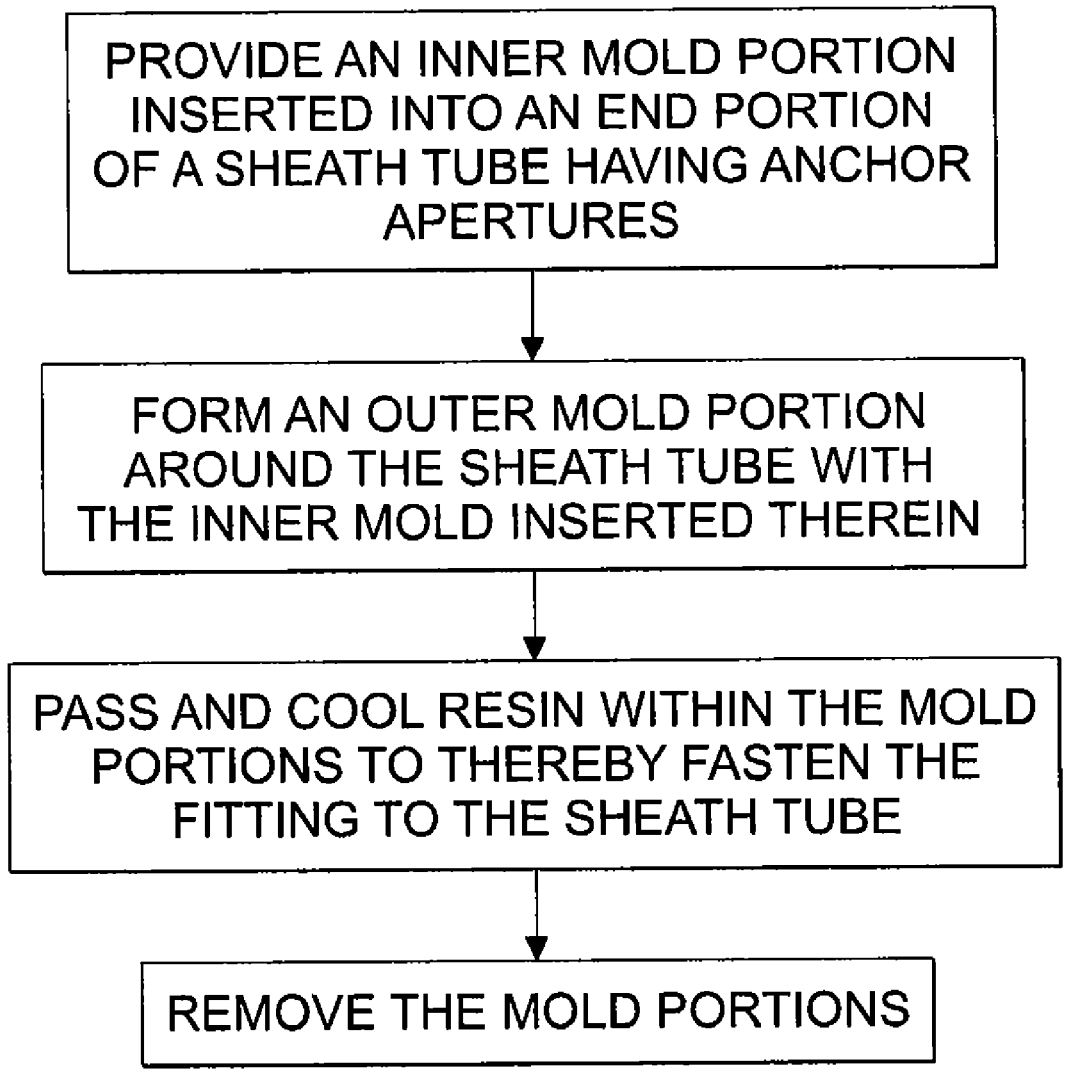
FIG. 7 is a flow chart of a method for making a sheath introducer of FIG. 1.

A method of manufacturing a peel-away introducer sheath adapted for use in the transcutaneous insertion of medical instrumentation according to an embodiment of the present invention is illustrated by the flow chart of FIG. 7. The method includes forming at least two anchor apertures 40 in an end portion of a peel-away sheath tube 30, molding fitting 20 around the end portion of sheath tube 30 by passing molten resin into a fitting mold and through at least two anchor apertures 40, and cooling the resin within the mold and at least two anchor apertures 40 to thereby fasten fitting 20 to the sheath tube 30.

The step of forming at least two anchor apertures in an end portion of sheath tube 30 preferably includes the step of forming six anchor apertures in an end portion of sheath tube 30. A number of ways exist to form the apertures, and would be known to those skilled in the art. One such way it to stamp or punch the tube so as to form the holes.

Molding fitting 20 around the end portion of sheath tube 30 forms a contiguous mechanical connection between the resin mold and at least two anchor apertures 40. The contiguous mechanical connection is formed because at least two anchor apertures 40 in sheath tube 30 have central axis B-B substantially perpendicular to longitudinal axis line A-A of sheath tube 30, and the apertures allow resin to flow between the inner and outer sides of the sheath tube and thereby form a solid, integral, one-piece connection with the central body.

As shown in FIG. 1, inner mold portion 50 is inserted into the aperture end of sheath tube to which the central body will be formed and connected. An outer mold portion (shown in FIG. 2) is then placed around sheath tube 30 having inner mold portion 50 inserted therein. The outer mold portion may be adapted to insert a resealable membrane into fitting 20. Molten resin is injected into the mold portions and allowed to cool. Upon removal of the outer mold portions and inner mold portion 50, fitting 20 is disposed on and connected to sheath tube 30.

Figure 5:
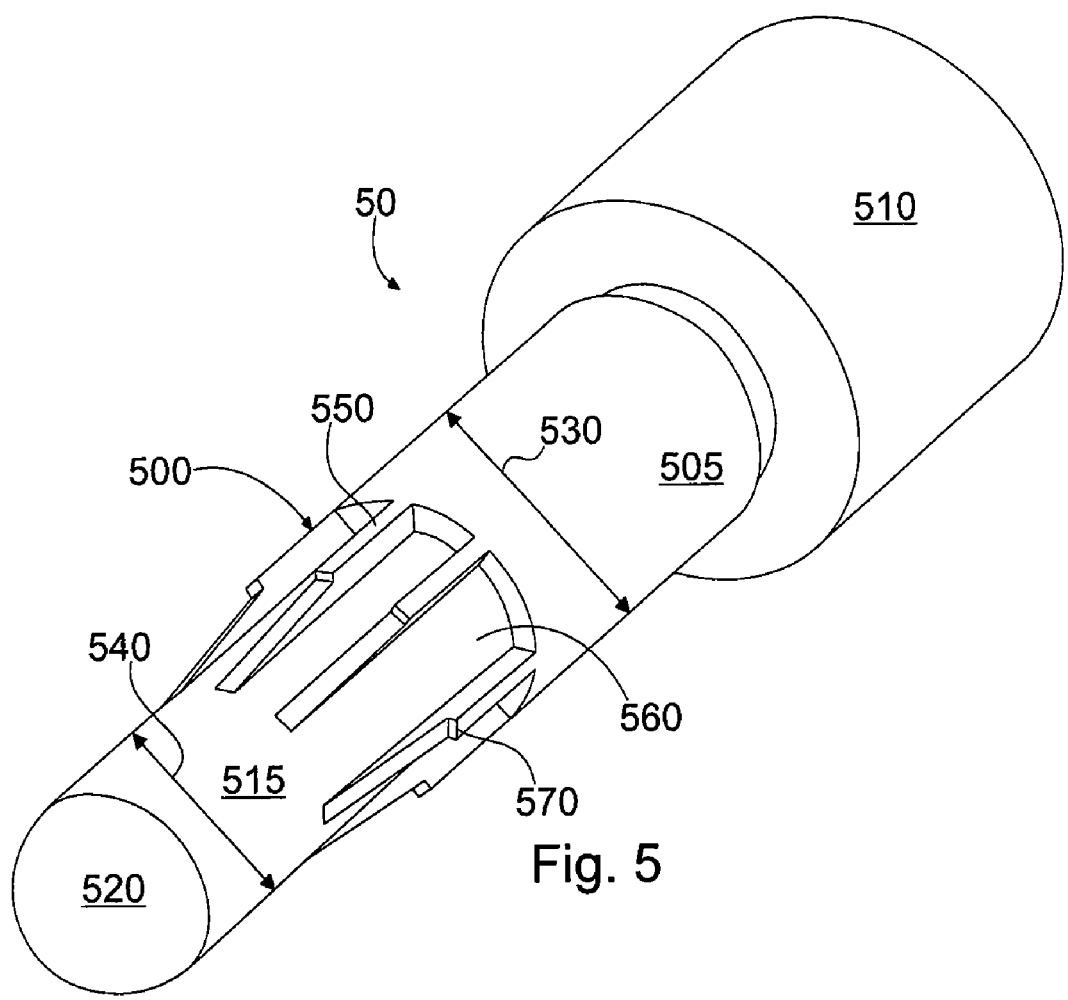
FIG. 5 is a perspective view of an embodiment of an inner mold portion.

FIG. 5 illustrates an exemplary inner mold portion according to an embodiment of the present invention. Inner mold portion 50 has shaft 500 having plug 510 at one end and a tapered or rounded end 520 at the other. Shaft 500 is generally of cylindrical or conical shape and has at least two portions, a plug end portion 505 and a tapered and portion 515. Tapered end portion 515 has a diameter 540 which is substantially similar to sheath tube 30 diameter 80. Plug end portion 505 has a diameter 530 that is larger than tapered end portion diameter 515. Bridging plug end portion 505 and tapered end portion 515 are radially outwardly projecting longitudinal ridges 550. Ridges 550 extend along shaft 500 and taper down and terminate at tapered end portion 515. Ridges 550 at their ends toward the end portion of inner mold portion 50 have substantially the same radius as the tapered end portion.

Ridges 550 define channels or furrows 560. Ridges 550 preferably have at least one notch 570 along their length. Notches 570 serve as a stop point for sheath tube 30. The relationship of inner mold portion 50, sheath tube 30, and fitting 20 is illustrated in FIG. 1. When inner mold portion 50 is initially inserted into sheath tube 30, tapered or rounded end 520 facilitates the insertion because tapered end portion diameter 540 is substantially similar to sheath tube diameter 80. In this manner, tapered end portion 515 frictionally fits into sheath 30. As inner mold portion 50 is further inserted into the end portion of sheath 30, ridges 550 define at least two channels 560 defining respective flow paths. Each of the flow paths is in fluid communication with an anchor aperture 40 (assuming the number of ridges equals the number of apertures). Thus, as molten resin flows into the mold for forming the fitting, the molten resin flows along the flow paths of channels 560 and through anchor apertures 40 to form fitting 20 and mechanically attach it to sheath tube 30.

Figure 6:
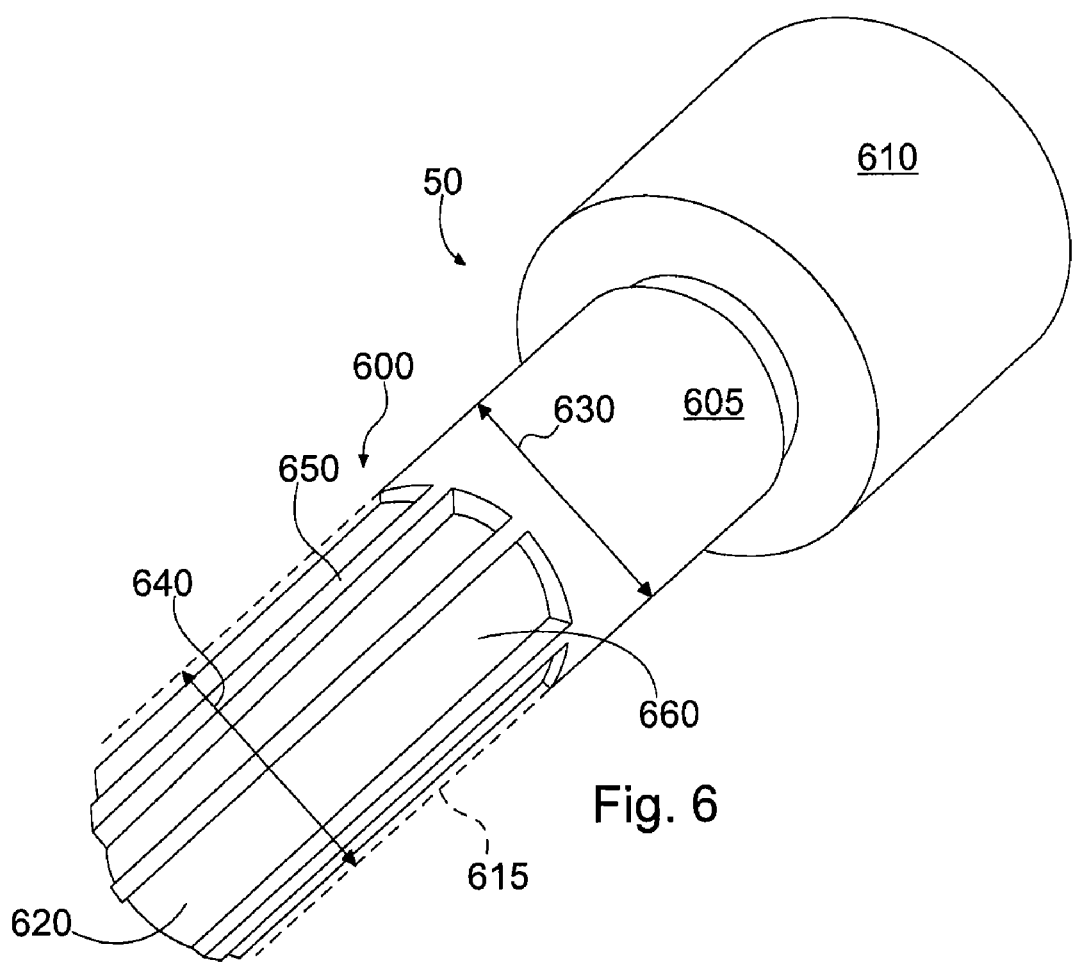
FIG. 6 is a perspective view of another embodiment of an inner mold portion.

FIG. 6 illustrates another embodiment of inner mold 50. The embodiment shown in FIG. 6 will be described in similar terms as discussed for the embodiment of inner mold portion shown in FIG. 5. According to the embodiment shown in FIG. 6, however, inner mold portion 50 has shaft 600 having plug 610 at one end and a tapered or rounded end 620 at the other. Shaft 600 is generally of cylindrical shape and has at least two portions, a plug end portion 605 and a tapered and portion 615. Tapered end portion 615 and plug end portion 605 have respective radial axis 640 and 630, which are substantially similar to radius 80 of sheath tube 30. Traveling substantially along shaft 600 from plug end portion 605 to tapered end portion 615 are channels or furrows 660 defined by ridges 650, which are substantially co-planar with tapered end portion 615 and plug end portion 605.

In other words, according to the embodiment shown in FIG. 6, shaft 600 is cylindrical in shape and maintains a uniform radius substantially along its length. Shaft 600 has tapered or rounded end 620 and disposed on the apposing end, plug 610. Along the length of shaft 600 are recesses or channels 660 that run substantially parallel to the longitudinal axis of shaft 600.

Inner mold portion 50, according to the embodiment shown in FIG. 6, is inserted into sheath tube 30. Shaft 600 of inner mold 50 has diameters 640 and 630 that are substantially similar to radius 80 of sheath tube 30 such that inner mold 50 frictionally fits into sheath tube 30. When inner mold 50 is inserted into sheath tube 30, channels or furrows 660 are aligned with anchor apertures 40 on sheath tube 30. Ridges 650 frictionally fit against the inner wall of sheath tube 30 and are coincidentally aligned with those portions of the sheath tube wall that are between anchor apertures 40. Ridges 650 and channels or furrows 660 thereby form a flow path through which molten resin is passed and forms fitting 20 in a mechanical connection with sheath tube 30. As understood by those skilled in the art, an additional means to prevent the resin from flowing into sheath tube 30 is necessary if the embodiment of FIG. 6 inner mold portion is used. Additional means may include quick cooling of the resin such that the resin is prevented from flowing passed tapered end 615 or a flow stop to prevent the resin from leaving the channels or furrows of inner mold portion 600.

Still yet a further embodiment of a method for making a tear-away introducer having a sheath tube splitable along at least one longitudinal axis of the tube and a fitting in a contiguous mechanical connection with the sheath includes forming at least two anchor apertures in an end portion of a peel-away sheath tube and inserting an inner mold portion having at least two channels defining respective flow paths into the end portion of the sheath. The anchor apertures may be formed before the inner mold is inserted into the sheath tube or after the inner mold is inserted into the sheath tube. The mold portion has at least two channels defining respective flow paths. The method further includes aligning the channels of the inner mold portion with the anchor apertures of the sheath whereby each of the flow paths are in fluid communication with an aperture, forming an outer mold portion around the inner mold portion inserted into the end portion of the sheath tube, passing molten resin into the outer mold portion whereby molten resin flows through the flow paths an the respective anchor aperture, and cooling the resin within the outer mold portion and the at least two anchor apertures to thereby fasten the fitting to the sheath tube in a contiguous mechanical connection.

A method of using a peel-away introducer sheath according to an embodiment of the present invention is as follows. Peel-away sheath introducer 10 is inserted in a patient using conventional percutaneous medical procedures including the combination of the introducer with a stylet of obturator. After insertion of the introducer sheath, the stylet or obturator is typically withdrawn. It will be appreciated that wings 40 provide additional structural integrity to introducer sheath 10 during insertion and manipulation of the device.

After removal of the stylet or obturator, a procedural device, such a pump or syringe, may be inserted into access lumen. This allows medicinal fluids, for example, heparin to be directly inserted into the vein or artery. If a syringe is inserted, it may be used to draw blood. Alternatively, if a pump is inserted, following the use of the pump, a catheter, such as a balloon catheter, could be inserted through peel-away introducer sheath 10. Resealable membrane 330 disposed within fitting 20 serves to prevent bleeding when introducer sheath is inserted into and artery or vein.

When the introducer sheath is to be removed, fitting 20 is broken at line of weakness 300 to separate fitting 20 into halves or as many pieces corresponding to the line of weakness. To break fitting 20, wings 40 are bent or twisted relative to each other, e.g., by rotating them in opposite radial directions. While a medical device is still inserted in the access lumen, the broken fitting is slowly separated forcing sheath tube 30 to also split. In the preferred embodiment, sheath tube 30 is polytetrafluoroethylene (PTFE) and does not need to be pre-scored. In alternative embodiments not using PTFE as the material of sheath tube 30, sheath tube 30 has a pre-formed tear line or score line that is substantially co-linear with line of weakness 300 of fitting 20. Thus, when fitting 20 is broken along line of weakness 300, sheath 30 also splits as a result of the force applied to break fitting 20.

Once fitting 20 is split and sheath tube 30 is split, sheath tube 30 may be extracted from the insertion by pulling the introducer sheath around and hubs of medical devices that remain in the transcutaneous insertion. In the preferred embodiment where sheath tube 30 is polyfluorotetraethylene (PTFE), because of the smooth surface of PTFE, removing sheath tube 30 does not tear or snag against the opening of the transcutaneous insertion.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A method of manufacturing a peel-away introducer sheath adapted for use in the transcutaneous insertion of medical instrumentation, said method comprising the steps of:
    forming at least two anchor apertures in an end portion of a peel-away sheath tube;
    molding a fitting around the end portion by passing a molten resin into a fitting mold, passing the molten resin around an exterior of the sheath tube, passing the molten resin into an interior space within the sheath tube, and passing molten resin through the at least two anchor apertures with the resin flowing between the exterior and the interior space through the apertures; and
    cooling the resin within the mold and the at least two anchor apertures to thereby fasten the fitting to the sheath tube.

2. The method of claim 1, wherein the molding step forms a contiguous mechanical connection between the resin mold and the at least two anchor apertures.

3. The method of claim 1, wherein the at least two anchor apertures have a central axis substantially perpendicular to a longitudinal axis of the sheath tube.

4. The method of claim 1, wherein the forming step comprises forming six anchor apertures.

5. The method of claim 1, wherein the fitting defines an opening having a radius substantially similar to the radius of the sheath tube.

6. The method of claim 1, wherein the sheath tube is scored on the end portion.

7. The method of claim 1, wherein the sheath is one of a thermoset or thermoplastic resin.

8. The method of claim 1, wherein the sheath is polytetrafluoroethylene.

9. The method of claim 1, wherein the fitting comprises at least two wing portions attached to a central body having at least one line of weakness.

10. The method of claim 1, wherein the molten resin is an injection-moldable thermoplastic resin.

11. The method of claim 1, wherein the molding step further comprises the step of inserting an inner mold portion into the end portion of the sheath, the mold portion having at least two channels defining respective flow paths, each of the flow paths in fluid communication with an aperture.

12. The method of claim 11, wherein the channels are defined by radially outwardly projecting longitudinal ridges along the inner mold portion.

13. The method of claim 12, wherein the ridges are tapered.

14. The method of claim 11 further comprising the step of forming an outer mold portion around the inner mold portion inserted into the end portion of the sheath tube.

15. The method of claim 14, wherein the outer mold portion is adapted to insert a resealable membrane in the fitting.

16. A method for making a tear-away introducer having a sheath tube splitable along at least one longitudinal axis of the tube and a fitting in a contiguous mechanical connection with the sheath, the method comprising the steps of:
    forming at least two anchor apertures in an end portion of a peel-away sheath tube;
    inserting an inner mold portion into the end portion of the sheath, the mold portion having at least two channels defining respective flow paths;
    aligning the channels of the inner mold portion with the anchor apertures of the sheath whereby each of the flow paths are in fluid communication with an aperture;
    forming an outer mold portion around the inner mold portion inserted into the end portion of the sheath tube;
    passing molten resin into the outer mold portion whereby molten resin flows through the flow paths an the respective anchor aperture; and
    cooling the resin within the outer mold portion and the at least two anchor apertures to thereby fasten the fitting to the sheath tube in a contiguous mechanical connection.

* * * * *